(12) United States Patent
Escribano et al.

(10) Patent No.: US 6,355,655 B1
(45) Date of Patent: Mar. 12, 2002

(54) HETEROCYCLIC SULPHONAMIDE DERIVATIVES

(75) Inventors: Ana Maria Escribano, Madrid (ES); Winton Dennis Jones, Carmel, IN (US); Paul Leslie Ornstein, Carmel, IN (US); Hamideh Zarrinmayeh, Carmel, IN (US); Dennis Michael Zimmerman, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/744,457

(22) PCT Filed: Jul. 28, 1999

(86) PCT No.: PCT/US99/17143

§ 371 Date: Jan. 23, 2001

§ 102(e) Date: Jan. 23, 2001

(87) PCT Pub. No.: WO00/06159

PCT Pub. Date: Feb. 10, 2000

Related U.S. Application Data

(60) Provisional application No. 60/094,770, filed on Jul. 31, 1998.

(51) Int. Cl.[7] ..................... A61K 31/445; C07D 211/18
(52) U.S. Cl. ......................................... 514/315; 546/232
(58) Field of Search ............... 546/236, 232; 514/315

(56) References Cited

U.S. PATENT DOCUMENTS

| | | | |
|---|---|---|---|
| 3,937,711 A | 2/1976 | Cook | 260/293.86 |
| 4,370,328 A | 1/1983 | Campbell et al. | 424/250 |
| 5,356,922 A | 10/1994 | Graeve et al. | 514/398 |
| 5,583,146 A | 12/1996 | Kimball et al. | 514/326 |
| 6,174,922 B1 | 1/2001 | Arnold et al. | 514/604 |

FOREIGN PATENT DOCUMENTS

| | | |
|---|---|---|
| EP | 0 811 375 A1 | 2/1995 |
| JP | 03-181475 | 8/1991 |
| WO | WO 98/12185 | 9/1996 |
| WO | WO 99/42458 | 2/1998 |

OTHER PUBLICATIONS

CA 128:204878p, "Preparation of pyrazinobenzothiazine derivatives and analogs for the treatment of inflammation and autoimmune diseases", vol. 128, No. 17, 1998, WO 9806720.*

Chem. Abstr. vol. 128, Feb. 19, 1998, No. 204878, Kaneko et al., Preparation of pyrinobenzothiazine derivatives and analogs for the treatment of inflammation and autoimmune diseases. WO9806720 A1.

U.S. application No. 09/355,605, Arnold et al., filed Feb. 4, 1997.

U.S. application No. 09/744,413, Arnold et al., filed Jul. 31, 1998.

U.S. application No. 09/744,414, Arnold et al., filed Jul. 31, 1998.

U.S. application No. 09/744,418, Arnold et al., filed Jul. 31, 1998.

U.S. application No. 09/744,419, Arnold et al., Jul. 31, 1998.

U.S. application No. 09/744,460, Cantrell et al., Jul. 31, 1998.

Beilstein Informationssyteme GmbH, Frankfurt, DE; XP002175340, Nov. 28, 1998.

* cited by examiner

*Primary Examiner*—Alan L. Rotman
*Assistant Examiner*—Binta Robinson
(74) *Attorney, Agent, or Firm*—Nelsen L. Lentz

(57) ABSTRACT

The present invention relates to the potentiation of glutamate receptor function using certain heterocyclic sulphonamide derivatives. It also relates to novel heterocyclic sulphonamide derivatives, to processes for their preparation and to pharmaceutical compositions containing them.

11 Claims, No Drawings

HETEROCYCLIC SULPHONAMIDE DERIVATIVES

This is a 371 of PCT/US99/17143 filed Jul. 28, 1999 which claims priority to U.S. Provisional Application No. 60/094,770 filed Jul. 31, 1998.

The present invention relates to the potentiation of glutamate receptor function using certain heterocyclic sulphonamide derivatives. It also relates to novel heterocyclic sulphonamide derivatives, to processes for their preparation and to pharmaceutical compositions containing them.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), alpha-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in c-AMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

AMPA receptors are assembled from four protein sub-units known as GluR1 to GluR4, while kainic acid receptors are assembled from the sub-units GluR5 to GluR7, and KA-1 and KA-2. Wong and Mayer, *Molecular Pharmacology* 44: 505–510, 1993. It is not yet known how these sub-units are combined in the natural state. However, the structures of certain human variants of each sub-unit have been elucidated, and cell lines expressing individual sub-unit variants have been cloned and incorporated into test systems designed to identify compounds which bind to or interact with them, and hence which may modulate their function. Thus, European patent application, publication number EP-A2-0574257 discloses the human sub-unit variants GluR1B, GluR2B, GluR3A and GluR3B. European patent application, publication number EP-A1-0583917 discloses the human sub-unit variant GluR4B.

One distinctive property of AMPA and kainic acid receptors is their rapid deactivation and desensitization to glutamate. Yamada and Tang, *The Journal of Neuroscience*, September 1993, 13(9): 3904–3915 and Kathryn M. Partin, *J. Neuroscience*, Nov. 1, 1996, 16(21): 6634–6647. The physiological implications of rapid desensitization, and deactivation if any, are unknown.

It is known that the rapid desensitization and deactivation of AMPA and/or kainic acid receptors to glutamate may be inhibited using certain compounds. This action of these compounds is often referred to in the alternative as "potentiation" of the receptors. One such compound, which selectively potentiates AMPA receptor function, is cyclothiazide. Partin et al., *Neuron*. Vol. 11, 1069–1082, 1993. Compounds which potentiate AMPA receptors, like cyclothiazide, are often referred to as ampakines.

International Patent Application Publication Number WO 9625926 discloses a group of phenylthioalkylsulphonamides, S-oxides and homologs which are said to potentiate membrane currents induced by kainic acid and AMPA.

Ampakines have been shown to improve memory in a variety of animal tests. Staubli et al., *Proc. Natl. Acad. Sci.*, Vol. 91, pp 777–781, 1994, *Neurobiology*, and Arai et al., *The Journal of Pharmacology and Experimental Therapeutics*, 278: 627–638, 1996.

It has now been found that cyclothiazide and certain heterocyclic sulphonamide derivatives potentiate agonist-induced excitability of human GluR4B receptor expressed in HEK 293 cells. Since cyclothiazide is known to potentiate glutamate receptor function in vivo, it is believed that this finding portends that the heterocyclic sulphonamide derivatives will also potentiate glutamate receptor function in vivo, and hence that the compounds will exhibit ampakine-like behavior.

Accordingly, the present invention provides a compound of the formula:

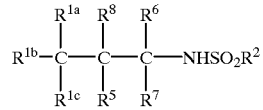

wherein:

$R^{1a}$ represents hydrogen or (1–4C)alkyl;

$R^{1b}$ and $R^{1c}$ together with the carbon atom to which they are attached form a 4 to 7 membered saturated heterocyclic ring containing as the hetero ring members a group $NR^a$ and a group X, wherein X is selected from the group consisting of —CH$_2$—, —NR$^b$—, —O— and —S—; and $R^a$ represents hydrogen, (1–4C)alkyl, optionally substituted aryl or optionally substituted aryl(1–4C)alkyl;

$R^b$ represents hydrogen, (1–4C)alkyl, optionally =substituted aryl or optionally substituted aryl (1–4C)alkyl;

$R^2$ represents (1–6C)alkyl, (3–6C)cycloalkyl, (1–6C)fluoroalkyl, (1–6C)chloroalkyl, (2–6C)alkenyl, (1–4C)alkoxy(1–4C)alkyl, phenyl which is unsubstituted or substituted by halogen, (1–4C)alkyl or (1–4C)alkoxy, or a group of formula $R^3R^4N$ in which $R^3$ and $R^4$ each independently represents (1–4C)alkyl or, together with the nitrogen atom to which they are attached form an azetidinyl, pyrrolidinyl, piperidinyl, morpholino, piperazinyl, hexahydroazepinyl or octahydroazocinyl group; and either (a) one or two of $R^5$, $R^6$, $R^7$ and $R^8$ represents hydrogen; (1–6C)alkyl; aryl(1–6C)alkyl; (2–6C) alkenyl; aryl(2–6C)alkenyl or aryl, or (b) two of $R^5$, $R^6$, $R^7$ and $R^8$ together with the carbon atom or carbon atoms to which they are attached form a (3–8C) carbocyclic ring; and the remainder of $R^5$, $R^6$, $R^7$ and $R^8$ represent hydrogen; or a pharmaceutically acceptable salt thereof.

According to another aspect, the present invention provides a method of potentiating glutamate receptor function in a mammal requiring such treatment, which comprises administering an effective amount of a compound of formula I, or a pharmaceutically acceptable salt thereof as defined herein.

According to another aspect, the present invention provides the use of a compound of formula I, or a pharmaceutically acceptable salt thereof as defined herein for the manufacture of a medicament for potentiating glutamate receptor function.

According to yet another aspect, the present invention provides the use of a compound of formula I or a pharmaceutically acceptable salt thereof as defined herein for potentiating glutamate receptor function.

In this specification, the term "potentiating glutamate receptor function" refers to any increased responsiveness of glutamate receptors, for example AMPA receptors, to glutamate or an agonist, and includes but is not limited to inhibition of rapid desensitisation or deactivation of AMPA receptors to glutamate.

A wide variety of conditions may be treated by the compounds of formula I and their pharmaceutically acceptable salts through their action as potentiators of glutamate receptor function. Such conditions include those associated with glutamate hypofunction, such as psychiatric and neurological disorders, for example cognitive disorders; neurodegenerative disorders such as Alzheimer's disease; age-related dementias; age-induced memory impairment; movement disorders such as tardive dyskinesia, Hungtington's chorea, myoclonus and Parkinson's disease; reversal of drug-induced states (such as cocaine, amphetamines, alcohol-induced states); depression; attention deficit disorder; attention deficit hyperactivity disorder; psychosis; cognitive deficits associated with psychosis; and drug-induced psychosis. The compounds of formula I may also be useful for improving memory (both short term and long term) and learning ability. The present invention provides the use of compounds of formula I for the treatment of each of these conditions.

The term "treating" (or "treat") as used herein includes its generally accepted meaning which encompasses prohibiting, preventing, restraining, and slowing, stopping, or reversing progression, severity, or a resultant symptom.

The present invention includes the pharmaceutically acceptable salts of the compounds defined by formula I. A compound of this invention can possess a sufficiently acidic, a sufficiently basic, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that the above salts may form hydrates or exist in a substantially anhydrous form.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of formula I can be resolved by one of ordinary skill in the art using standard techniques well known in the art, such as those described by J. Jacques, et al., "Enantiomers, Racemates, and Resolutions", John Wiley and Sons, Inc., 1981. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

As used herein, the term "aryl" includes phenyl and a polycyclic aromatic carbocyclic ring such as naphthyl.

The term "optionally substituted" as used in the term "optionally substituted aryl" or "optionally substituted aryl (1–4C)alkyl" herein signifies that the aryl group is unsubstituted or substituted by one or more (for example one or two) substituents, said substituents being selected from atoms and groups which, when present in the compound of formula I, do not prevent the compound of formula I from functioning as a potentiator of glutamate receptor function.

Examples of substituents which may be present in an optionally substituted aryl group include halogen; nitro; cyano; (1–4C)alkyl; (1–4C)alkoxy; halo(1–4C)alkyl; and a group of formula —(L$^1$)$_x$—X$^1$—(L$^2$)$_y$—R$^9$ in which each of L$^1$ and L$^2$ independently represents (1–4C)alkylene, one of x and y is 0 and the other is 0 or 1, X$^1$ represents a bond, O, S, NH, CO, CONH or NHCO, and R$^9$ represents a phenyl group that is unsubstituted or substituted by one or two of halogen, (1–4C)alkyl and (1–4C)haloalkyl.

Unless specified otherwise, any alkyl group may be unbranched or branched. The term "(1–6C)alkyl" includes "(1–4C)alkyl". Examples of particular values for a (1–6C) alkyl group include methyl, ethyl, propyl, isopropyl, butyl, isobutyl, tert-butyl, pentyl and hexyl.

The term (1–4C)alkylene includes (2–4C)alkylene. Examples of particular values are methylene and ethylene.

The 4 to 7 membered saturated heterocyclic ring containing a group NR$^a$ and a group X, wherein X is selected from the group consisting of —CH$_2$—, —NR$^b$—, —O— and —S— may be selected, for example, from azetidinyl, pyrrolidinyl, piperidinyl, morpholinyl, thiomorpholinyl, piperazinyl, hexahydropyrimidyl, tetrahydro-1,3-oxazinyl, tetrahydro-1,3-thiazinyl and hexahydroazepinyl.

Examples of 4 to 7 membered saturated heterocyclic rings are those wherein R$^{1b}$ and R$^{1c}$ together with the carbon atom to which they are attached are selected from the group consisting of:

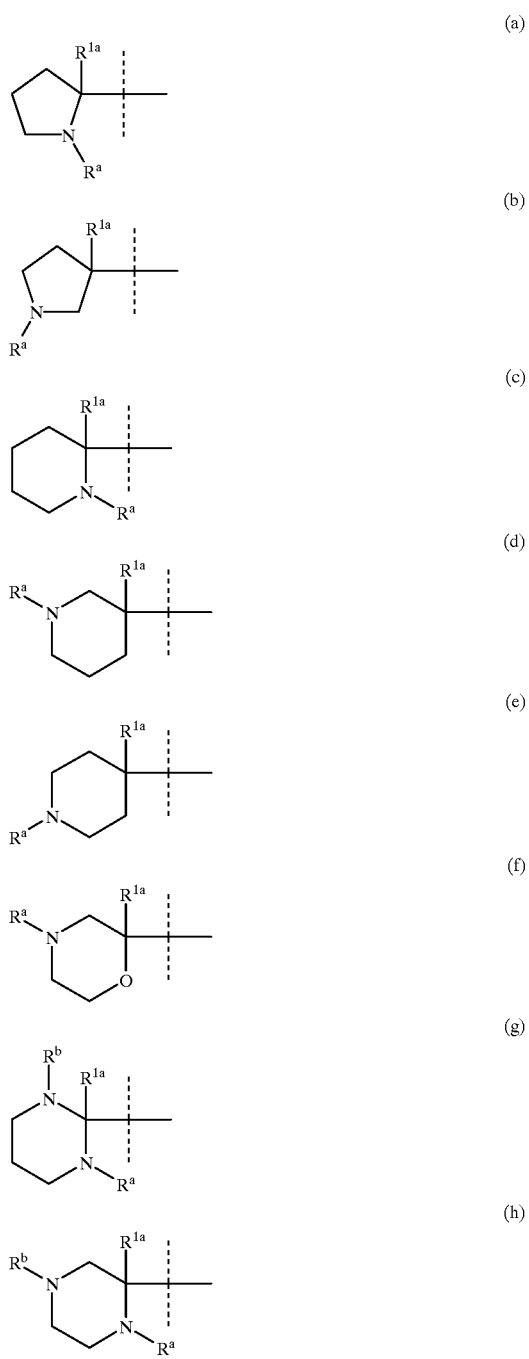

-continued

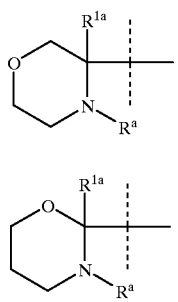

(i)

(j)

wherein $R^a$ represents hydrogen, (1–4C)alkyl, optionally substituted aryl or optionally substituted aryl(1–4C)alkyl; and $R^b$ represents hydrogen, (1–4C)alkyl, optionally substituted aryl or optionally substituted aryl(1–4C)alkyl.

Examples of particular values for $R^a$ and $R^b$ are methyl, ethyl, propyl, phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2,3-difluorophenyl, 2,4-difluorophenyl, 3,4-dichlorophenyl, 3,5-dichlorophenyl, 4-cyanophenyl, 3-nitrophenyl, 2-methylphenyl, 4-methylphenyl, 4-ethylphenyl, 3-propylphenyl, 4-t-butylphenyl, 2-trifluoromethylphenyl, 3-trifluoromethylphenyl, 4-trifluoromethylphenyl, 2-fluoro-4-trifluoromethylphenyl, 2-methoxyphenyl, 3-methoxyphenyl, 4-methoxyphenyl and benzyl.

A preferred value for the 4 to 7 membered saturated heterocyclic ring is a group of formula (a) above, such as N-methyl-2-pyrrolidinyl, or a group of formula (e) above, such as 1-(2-fluorophenyl)piperidin-4-yl.

An alkenyl group, for example as in (2–6C)alkenyl or aryl(2–6C)alkenyl may be branched or unbranched. Examples of particular values are vinyl and prop-2-enyl.

The term (3–8C)cycloalkyl includes (3–6C)cycloalkyl. Examples of particular values for (3–8C)cycloalkyl are cyclopropyl, cyclobutyl, cyclopentyl and cyclohexyl.

The term "halo(1–6C)alkyl" includes halo(1–4C)alkyl, (1–6C)fluoroalkyl, such as trifluoromethyl or 2,2,2-trifluoroethyl, and (1–6C)chloroalkyl, such as chloromethyl.

The term "halogen" includes fluorine, chlorine and bromine.

An example of a particular value for $R^{1a}$ is hydrogen.

Examples of values for $R^2$ are methyl, ethyl, propyl, 2-propyl, butyl, 2-methylpropyl, cyclohexyl, trifluoromethyl, 2,2,2-trifluoroethyl, chloromethyl, ethenyl, prop-2-enyl, methoxyethyl, phenyl, 4-fluorophenyl, or dimethylamino.

Preferably $R^2$ is ethyl, 2-propyl or dimethylamino.

Preferably $R^3$ and $R^4$ each represent methyl.

Examples of a (1–6C)alkyl group represented by $R^5$, $R^6$, $R^7$ and $R^8$ are methyl, ethyl and propyl. An example of an aryl(1-C)alkyl group is benzyl. An example of a (2–6C) alkenyl group is prop-2-enyl. An example of a (3–8C) carbocyclic ring is a cyclopropyl ring.

Preferably $R^6$ and $R^7$ each represents hydrogen.

Preferably $R^5$ and $R^8$ each independently represents hydrogen or (1–4C)alkyl, or together with the carbon atom to which they are attached form a (3–8C) carbocyclic ring.

More preferably $R^8$ represents methyl or ethyl and $R^5$ represents hydrogen or methyl, or $R^5$ and $R^8$ together with the carbon atom to which they are attached form a cyclopropyl ring.

Especially preferred are compounds in which $R^8$ represents methyl and $R^5$, $R^6$ and $R^7$ each represents hydrogen.

The compounds of formula I may be prepared by reacting a compound of formula

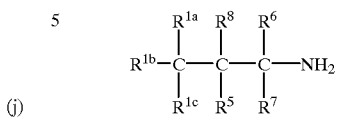

II with a compound of formula

 III in which Z represents a leaving atom or group, followed where necessary and/or desired by forming a pharmaceutically acceptable salt.

The leaving atom or group represented by Z may be, for is example, a halogen atom such as a chlorine or bromine atom.

The reaction is conveniently performed in the presence of a base, for example an alkali metal hydroxide such as sodium hydroxide, an alkali metal carbonate such as potassium carbonate, a tertiary amine such as triethylamine or 1,8-diazabicyclo[5.4.0]undec-7-ene.

Suitable solvents include halogenated hydrocarbons such as dichloromethane.

The reaction is conveniently performed at a temperature in the range of from −20 to 100° C., preferably from −5 to 50° C.

The compounds of formula II are known or may be prepared by reducing a corresponding nitrile or amide, for example using a borane, such as borane dimethyl sulfide, or lithium aluminium hydride. Convenient solvents for the reduction include ethers, such as tetrahydrofuran and diethyl ether.

Some of the nitriles and amides used as starting materials may conveniently be prepared by treatment of a nitrile of formula

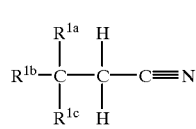

IV or an ester of formula

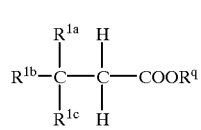

V in which is an ester residue, such as a (1–6C)alkyl group, with a strong base, for example an alkali metal amide such as sodium or lithium bis(trimethylsilyl)amide and a compound of formula $R^5Z^1$ or $R^8Z^1$ in which $Z^1$ represents a leaving atom or group, such as an iodine atom. Convenient solvents include ethers, such as tetrahydrofuran. The temperature is conveniently in the range of from −78 to 25° C. The esters are then converted to the amides by hydrolysis, for example using sodium or potassium hydroxide in an aqueous alcohol to afford an acid, and conversion of the acid to an amide, for example by reaction of the acid with thionyl chloride followed by aqueous ammonia.

Alternatively, a compound of formula

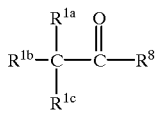

VI may be reacted with toluenesulfonylmethyl isocyanide in the presence of a strong base, such as potassium t-butoxide. Suitable solvents include ethyleneglycol dimethyl ether (DME). The reaction is conveniently performed at a temperature in the range of from −78 to 25° C.

It will be appreciated that in the processes described above, it may be preferable to protect the nitrogen atom in the groups represented by $NR^a$ and $NR^b$ when $R^a$ or $R^b$ is hydrogen. Suitable protecting groups include acyl groups, such as acetyl or benzoyl, and acyloxy groups, such as t-butoxycarbonyl. A t-butoxycarbonyl may conveniently be removed using trifluoroacetic acid.

The ability of compounds of formula I to potentiate glutamate receptor-mediated response may be determined using fluorescent calcium indicator dyes (Molecular Probes, Eugene, Oreg., Fluo-3) and by measuring glutamate-evoked efflux of calcium into GluR4 transfected HEK293 cells, as described in more detail below.

In one test, 96 well plates containing confluent monolayers of HEK cells stably expressing human GluR4B (obtained as described in European Patent Application Publication Number EP-A1-583917) are prepared. The tissue culture medium in the wells is then discarded, and the wells are each washed once with 200 µl of buffer (glucose, 10 mM, sodium chloride, 138 mM, magnesium chloride, 1 mM, potassium chloride, 5 mM, calcium chloride, 5 mM, N-[2-hydroxyethyl]-piperazine-N-[2-ethanesulfonic acid], 10 mM, to pH 7.1 to 7.3). The plates are then incubated for 60 minutes in the dark with 20 µM Fluo3-AM dye (obtained from Molecular Probes Inc, Eugene, Oreg.) in buffer in each well. After the incubation, each well is washed once with 100 µl buffer, 200 µl of buffer is added and the plates are incubated for 30 minutes.

Solutions for use in the test are also prepared as follows. 30 µM, 10 µM, 3 µM and 1 µM dilutions of test compound are prepared using buffer from a 10 mM solution of test compound in DMSO. 100 µM cyclothiazide solution is prepared by adding 3 µl of 100 mM cyclothiazide to 3 ml of buffer. Control buffer solution is prepared by adding 1.5 µl DMSO to 498.5 µl of buffer.

Each test is then performed as follows. 200 µl of control buffer in each well is discarded and replaced with 45 µl of control buffer solution. A baseline fluorescent measurement is taken using a FLUOROSKAN II fluorimeter (Obtained from Labsystems, Needham Heights, Mass., USA, a Division of Life Sciences International Plc). The buffer is then removed and replaced with 45 µl of buffer and 45 µl of test compound in buffer in appropriate wells. A second fluorescent reading is taken after 5 minutes incubation. 15 µl of 400 µM glutamate solution is then added to each well (final glutamate concentration 100 µM), and a third reading is taken. The activities of test compounds and cyclothiazide solutions are determined by subtracting the second from the third reading (fluorescence due to addition of glutamate in the presence or absence of test compound or cyclothiazide) and are expressed relative to enhance fluorescence produced by 100 µM cyclothiazide.

In another test, HEK293 cells stably expressing human GluR4 (obtained as described in European Patent Application Publication No. EP-A1-0583917) are used in the electro-physiological characterization of AMPA receptor potentiators. The extracellular recording solution contains (in mM): 140 NaCl, 5 KCl, 10 HEPES, 1 $MgCl_2$, 2 $CaCl_2$, 10 glucose, pH=7.4 with NaOH, 295 mOsm $kg^{-1}$. The intracellular recording solution contains (in M): 140 CsCl, 1 $MgCl_2$, 10 HEPES, (N-[2-hydroxyethyl]piperazine-$N^1$-[2-ethanesulfonic acid]) 10 EGTA (ethylene-bis (oxyethylenenitrilo)tetraacetic acid), pH=7.2 with CsOH, 295 mOsm $kg^{-1}$. With these solutions, recording pipettes have a resistance of 2–3 MΩ. Using the whole-cell voltage clamp technique (Hamill et al.(1981)Pflügers Arch., 391: 85–100), cells are voltage-clamped at −60 mV and control current responses to 1 mM glutamate are evoked. Responses to 1 mM glutamate are then determined in the presence of test compound. Compounds are deemed active in this test if, at a test concentration of 10 µM, they produce a greater than 30% increase in the value of the current evoked by 1 mM glutamate.

In order to determine the potency of test compounds, the concentration of the test compound, both in the bathing solution and co-applied with glutamate, is increased in half log units until the maximum effect was seen. Data collected in this manner are fit to the Hill equation, yielding an $EC_{50}$ value, indicative of the potency of the test compound. Reversibility of test compound activity is determined by assessing control glutamate 1 mM responses. Once the control responses to the glutamate challenge are re-established, the potentiation of these responses by 100 µM cyclothiazide is determined by its inclusion in both the bathing solution and the glutamate-containing solution. In this manner, the efficacy of the test compound relative to that of cyclothiazide can be determined.

According to another aspect, the present invention provides a pharmaceutical composition, which comprises a compound of formula I or a pharmaceutically acceptable salt thereof as defined hereinabove and a pharmaceutically acceptable diluent or carrier.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 1 mg to about 500 mg, more preferably about 5 mg to about 300 mg (for example 25 mg) of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1

Hard gelatin capsules are prepared using the following ingredients:

|   | Quantity (mg/capsule) |
|---|---|
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

Tablets each containing 60 mg of active ingredient are made as follows:

|   |   |
|---|---|
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

As used herein the term "patient" refers to a mammal, such as a mouse, guinea pig, rat, dog or human. It is understood that the preferred patient is a human.

As used herein the term "effective amount" refers to the amount or dose of the compound which provides the desired effect in the patient under diagnosis or treatment.

The particular dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

The following Preparations and Examples illustrate the invention.

PREPARATION 1

N-[2-[N-Tert-butoxycarbonyl-4-piperidinyl]propyl] 2-propanesulfonamide

A. 4-(Cyanomethylidene)-1-piperidinecarboxylic acid, 1,1-dimethylethyl ester: To a suspension of 2.8 g (60% by weight in oil, 70 mmol) of sodium hydride (washed three times with hexane) in 100 ml of THF, was added 12.4 g (70 mmol) of diethyl (cyanomethyl)phosphonate neat at ambient temperature. The mixture was stirred for 30 min at ambient temperature and then 10 g (50 mmol) of N-tert-butoxycarbonyl-4-piperidone in 30 ml of THF was added. After 30 min, the reaction was quenched with $NH_4Cl$ saturated solution and extracted three times with diethyl ether. The organic phase was dried over $Na_2SO_4$, filtered and concentrated in vacuo. Chromatography (500 g of silica gel, 20% ethyl acetate/hexane) of the residue afforded 10.6 g (95%) of the title compound.

B. 4-(Cyanomethyl)-1-piperidinecarboxylic acid, 1,1-dimethylethyl ester: A solution of 10 g (45 mmol) of material from step A in 270 ml of ethanol was hydrogenated with 1.2 g of 5% Pd/C at ambient temperature and 60 psi for 2 h. The mixture was filtered through celite and concentrated in vacuo to afford 8.85 g (88%) of the title compound.

C. 4-(2-Cyanoethyl)-1-piperidinecarboxylic acid, 1,1-dimethylethyl ester: To a solution of 3 g (13.4 mmol) of material from step B in 45 ml of THF at −78° C. was added 14.7 ml of a 1M solution of lithium bis(trimethylsilyl)amide in THF (14.7 mmol). The mixture was stirred for 30 min and then 2.1 g (14.7 mmol) of iodomethane was added at −78° C. After stirring for 1 h., the bath was removed and the mixture was stirred at ambient temperature for 30 min. The reaction was quenched with $NH_4Cl$ saturated solution and extracted three times with diethyl ether. The organic phase was dried over $Na_2SO_4$, filtered and concentrated in vacuo. Chromatography (150 g of silica gel, 20% ethyl acetate/hexane) of the residue afforded 2.8 g (88%) of the title compound.

D. N-[2-[N-tert-butoxycarbonyl-4-piperidinyl]propyl]2-propanesulfonamide: To a ambient temperature suspension of 175 mg (4.61 mmol) of lithium aluminum hydride in 7 ml of diethyl ether was added dropwise 1.0 g (4.19 mmol) of material from step C in 7 ml of diethyl ether. The mixture was stirred for 2 h. $Na_2SO_4 \cdot 10H_2O$ was added, and the mixture stirred for 30 min at ambient temperature. The solid was filtered and the organic solution was concentrated in vacuo. The crude was dissolved in dichloromethane (14 ml) and cooled to 0° C., triethylamine 1.75 ml (12.57 mmol) was added, followed by isopropylsulfonyl chloride (0.61 ml, 5.45 mmol). The ice-bath was removed and the solution was stirred at ambient temperature for 4 h. The organic solution was washed with 1N hydrochloric acid, sodium bicarbonate saturated solution, brine, dried over $Na_2SO_4$ filtered and concentrated in vacuo. Chromatography (100 g of silica gel, 33% ethyl acetate/hexane) of the residue afforded 230 mg (16%) of the title compound. Ion Electrospray Mass Spectrum: M+1=349

PREPARATION 2

N-[2-(4-Piperidinyl)propyl]2-propanesulfonamide, Trifluoroacetate

To a 0° C. solution of 200 mg (0.57 mmol) of material prepared in Preparation 1 in 2 ml of dichloromethane was added dropwise 0.44 ml (5.7 mmol) of trifluoroacetic acid. The ice-bath was removed and the mixture stirred at ambient temperature overnight. The solution was concentrated in vacuo to afford the title compound (203 mg). Ion Electrospray Mass Spectrum: M+1−$C_2HF_3O_2$=249

PREPARATION 3

N-[2-(N-Benzoyl-4-piperidinyl)propyl]2-propanesulfonamide

To 0° C. solution of 25 mg (0.069 mmol) of material prepared in Preparation 2 in 1 ml of dichloromethane, was added triethylamine 21 μl (0.15 mmol), followed by benzoyl chloride (10 μl, 0.083 mmol). The ice-bath was removed and the solution was stirred at ambient temperature overnight. The organic solution was washed with 1 N hydrochloric acid, sodium bicarbonate saturated solution, brine, dried over $Na_2SO_4$ filtered and concentrated in vacuo. Chromatography (20 g of silica gel, 33% ethyl acetate/hexane) of the residue afforded 15 mg (61%) of the title compound. Field Desorption Mass Spectrum: M=352.

PREPARATION 4

2-(N-Methyl-2-pyrrolidinyl)proprionitrile

2-Acetyl-N-methylpyrrolidine 0.979g (7.7 mmol) and toluenesulfonylmethyl isocyanide 2.3 g (11.5 mmol) are dissolved in 50 mL of dry DME and cooled to −78° C. while stirring under $N_2$. To this mixture is added dropwise a solution of potassium t-butoxide 1.75 g (15.4 mmol) in 15 mL of hot t-butanol. The reaction mixture is stirred at −78° C. for 3 h then poured into 50 mL of $H_2O$ and extracted with 150 mL of dichloromethane and 150 mL of EtOAc. The organic layers are combined, washed with saturated $NaHCO_3$ and saturated NaCl, dried and concentrated in vacuo. Purification by chromatography gives the title compound.

PREPARATION 5

2-(N-Methyl-2-pyrrolidinyl)propylamine dihydrochloride

To a stirred solution of the product of Preparation 4 (0.88 g, 6.4 mmol) in 30 mL of tetrahydrofuran (THF) at ambient temperature under $N_2$ is added borane dimethyl sulfide (3.7 mL 7.3 mmol) of a 2.0M solution in THF. The mixture is heated under reflux for 4 h then cooled to ambient temperature. Methanolic HCl is added and the resulting solid precipitate is used without further purification.

EXAMPLE 1

N-[2-(N-(2-fluorophenyl)-4-piperidinyl)propyl]2-propanesulfonamide

A. 2-(4-piperidinyl)propanenitrile: To a 0° C. solution of 2.1 g (8.8 mmol) of material prepared in Preparation 1 (step C) in 29 ml of dichloromethane was added dropwise 2 ml (26.4 mmol) of trifluoroacetic acid. The ice-bath was removed and the mixture stirred at ambient temperature overnight. To the solution was added 0.5 ml (6.5 mmol) of trifluoroacetic acid and stirred for 2 h. A saturated solution of sodium bicarbonate was added, and extracted three times with dichloromethane. The organic phase was dried over $Na_2SO_4$, filtered and concentrated in vacuo. Afforded 1.18 g (97%) of the title compound.

B. 2-(N-(2-fluorophenyl)-4-piperidinyl)propanenitrile: To a suspension of 1.0 g (7.23 mmol) of the material prepared in step A, 0.7 ml (6.09 mmol) of 1-fluoro-2-iodobenzene, 1.17 g (12.18 mmol) of sodium tert-butoxide in 15 ml of dioxane and 5 ml of toluene, 111 mg (0.12 mmol) of $Pd_2$ $(dba)_3$ (tris (dibenzylideneacetone) dipalladium(0)) and 75 mg (0.12 mmol) of R(+)-BINAP (2,2'-bis (diphenylphosphino)-1,1'-binaphthyl) were added and the mixture was heated at 108° C. in a seal tube overnight. Brine was added and extracted three times with diethyl ether. The organic phase was dried over $Na_2SO_4$, filtered and concentrated in vacuo. Chromatography (300 g of silica gel, 20% ethyl acetate/hexane) of the residue afforded 330 mg (24%) of the title compound.

C. 2-(N-(2-fluorophenyl)-4-piperidinyl)propaneamine, hydrochloride: To an ambient temperature solution of 330 mg (1.47 mmol) of material prepared in step B in 5 ml of THF was added dropwise 0.16 ml of a 10 M solution borane-methyl sulfide complex (1.62 mmol) in THF. The mixture was heated at reflux for 2 h. A saturated solution of hydrochloric acid in methanol (16 ml) was added, and stirred for 10 min. The solution was concentrated in vacuo. Diethyl ether was added, and the white solid was filtered. Afforded 390 mg (97%) of the title compound D. N-[2-(N-(2-fluorophenyl)-4-piperidinyl)propyl]2-propanesulfonamide: A solution of the material from step C, 390 mg, (1.42 mmol) in dichloromethane (5 ml) was cooled to 0° C., triethylamine 0.45 ml (3.26 mmol) was added, followed by isopropylsulfonyl chloride (0.20 ml, 1.84 mmol). The ice-bath was removed and the solution was stirred at ambient temperature for 4 h. The organic solution was washed with 1 N hydrochloric acid, sodium bicarbonate saturated solution, brine, dried over $Na_2SO_4$ filtered and concentrated in vacuo. Chromatography (30 g of silica gel, 15% ethyl acetate/hexane) of the residue afforded 153 mg (31%) of the title compound. Analysis calculated for $C_{17}H_{28}N_2O_2SF$: % C, 59.45; % H, 8.22; % N, 8.16. Found: % C, 59.94; % H, 7.58; % N, 7.38. Ion Electrospray Mass Spectrum: M+1=343.

EXAMPLE 2

N-(2-(N-Methyl-2-pyrrolidinyl)propyl) 2-propanesulfonamide

To a stirred suspension of the product of Preparation 5 (2.69 g, 12.5 mmol) in 50 mL of dichloromethane under $N_2$ at 0° C. is added 1,8-diazabicyclo[5.4.0]undec-7-ene (DBU) (3.8 mL 27.5 mmol). The reaction mixture is stirred for 30 minutes, then isopropylsulfonyl chloride (1.7 mL, 15.0 mmol) is added dropwise. The reaction mixture is then allowed to warm to ambient temperature and stirred for 4 h. The reaction is then diluted with $H_2O$ and the layers are separated. The aqueous layer is extracted with dichloromethane and the combined organic extracts washed with saturated NaCl, dried over $MgSO_4$ and filtered. Evaporation of the filtrate and chromatography of the residue gives the title compound.

We claim:

1. A compound of the formula:

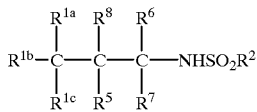

wherein $R^{1a}$ represents hydrogen or (1–4C)alkyl;

$R^{1b}$ and $R^{1c}$ together with the carbon atom to which they are attached form a saturated heterocyclic ring selected from the following:

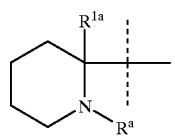

(c)

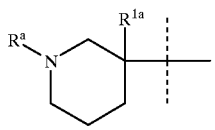

(d)

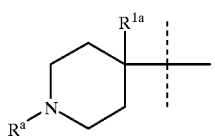

(e)

and $R^a$ represents an optionally substituted aryl wherein the aryl is optionally substituted with halogen;

$R^2$ represents (1–6C)alkyl; and $R^5$ represents (1–6C)alkyl;

$R^6$ and $R^7$ represent hydrogen; and $R^8$ represents hydrogen, (1–6C)alkyl, (2–6C)alkenyl, or aryl(2–6C)alkenyl;

or a pharmaceutically acceptable salt thereof.

2. A compound as claimed in claim 1, wherein $R^{1b}$ and $R^{1c}$ together with the carbon atom to which they are attached form a group of formula

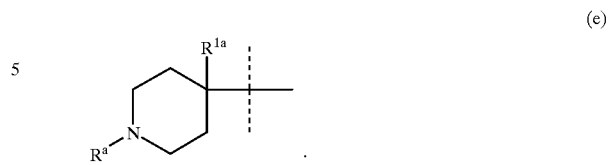

(e)

3. A compound according to claim 2, wherein $R^a$ is selected from phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2,3-difluorophenyl, 2,4difluorophenyl, 3,4-dichlorophenyl, and 3,5-dichlorophenyl.

4. A compound according to claim 3, in which $R^2$ represents methyl, ethyl, propyl, 2-propyl, butyl, or 2-methylpropyl.

5. A compound as claimed in claim 4, in which $R^2$ represents ethyl or 2-propyl.

6. A compound as claimed in claim 5, wherein $R^5$ represents (1–4C) alkyl and $R^8$ represents hydrogen or (1–4C)alkyl.

7. A compound as claimed in claim 6, wherein $R^8$ represents hydrogen and $R^5$ represents methyl.

8. A pharmaceutical composition, which comprises a compound as claimed in claim 1 and a pharmaceutically acceptable diluent or carrier.

9. A method of treating a cognitive disorder, a neurodegenerative disorder; age-related dementia; age-induced memory impairment; a movement disorder, attention deficit disorder; attention deficit hyperactivity disorder; psychosis; cognitive deficits associated with psychosis; or drug-induced psychosis in a patient, which comprises administering to a patient in need thereof an effective amount of a compound as claimed in claim 1.

10. A method for improving memory or learning ability in a patient, which comprises administering to a patient in need thereof an effective amount of a compound as claimed in claim 1.

11. A compound according to claim 7 which is N-[2-(N-(2-fluorophenyl)-4-piperidinyl)propyl]2-propanesulfonamide.